(12) United States Patent
Kohn et al.

(10) Patent No.: US 8,461,289 B2
(45) Date of Patent: Jun. 11, 2013

(54) BIORESORBABLE POLYMERS SYNTHESIZED FROM MONOMER ANALOGS OF NATURAL METABOLITES

(75) Inventors: Joachim B. Kohn, Piscataway, NJ (US); Durgadas Bolikal, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/482,667

(22) Filed: May 29, 2012

(65) Prior Publication Data

US 2012/0302719 A1    Nov. 29, 2012

Related U.S. Application Data

(60) Continuation of application No. 13/063,944, filed as application No. PCT/US2009/057216 on Sep. 16, 2009, application No. 13/482,667, which is a continuation-in-part of application No. 13/183,051, filed on Jul. 14, 2011, which is a division of application No. 11/873,979, filed on Oct. 17, 2007, now Pat. No. 8,008,528, which is a continuation of application No. PCT/US2007/081571, filed on Oct. 16, 2007.

(60) Provisional application No. 61/097,494, filed on Sep. 16, 2008, provisional application No. 60/852,471, filed on Oct. 17, 2006.

(51) Int. Cl.
*C08G 64/00*    (2006.01)
*C08G 63/02*    (2006.01)

(52) U.S. Cl.
USPC .......... 528/310; 424/422; 528/208; 564/170; 568/774

(58) Field of Classification Search
USPC .......... 424/422; 528/208; 564/170; 568/774
See application file for complete search history.

(56) References Cited

U.S. PATENT DOCUMENTS

2011/0275782 A1 * 11/2011 Kohn et al. ............... 528/208

* cited by examiner

*Primary Examiner* — Terressa Boykin
(74) *Attorney, Agent, or Firm* — Fox Rothschild LLP (57) ABSTRACT

New bioresorbable polymers are synthesized from monomer analogs of natural metabolites In particular, polymers are polymerized from analogs of amino acids that contribute advantageous synthesis, processing and material properties to the polymers prepared therefrom, including particularly advantageous degradation profiles.

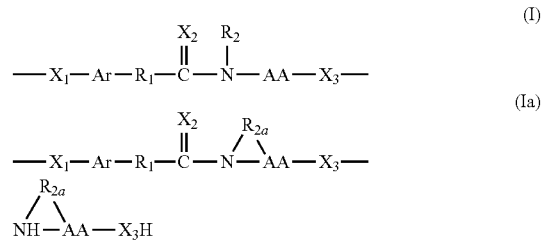

18 Claims, 1 Drawing Sheet

BIORESORBABLE POLYMERS SYNTHESIZED FROM MONOMER ANALOGS OF NATURAL METABOLITES

CROSS-REFERENCE TO RELATED APPLICATION

The present application is a Continuation of U.S. application Ser. No. 13/063,944, filed on Mar. 15, 2011, which is the U.S. National Phase of International Patent Application Serial No. PCT/US09/57216, designating the United States and filed on Sep. 16, 2009, and which claims priority benefit under 35 U.S.C. §119(e) of U.S. Provisional Patent Application Ser. No. 61/097,494, filed on Sep. 16, 2008. The present application is also a Continuation-in-Part of U.S. application Ser. No. 13/183,051, filed on Jul. 14, 2011, which is a Divisional of U.S. application Ser. No. 11/873,979, filed on Oct. 17, 2007, now U.S. Pat. No. 8,008,528, issued on Aug. 30, 2011, and which claims priority under 35 U.S.C. §119(e) to U.S. Provisional Patent Application Ser. No. 60/852,471, filed on Oct. 17, 2006, and which also claims priority under 35 U.S.C. §120 to International Patent Application Serial No. PCT/US07/81571 designating the United States and filed on Oct. 16, 2007. The entire disclosures of all of the above applications are incorporated herein by reference.

BACKGROUND OF THE INVENTION

The present invention relates to new bioresorbable polymers synthesized from monomer analogs of natural metabolites. In particular, the present invention relates to polymers polymerized from analogs of amino acids that contribute advantageous synthesis, processing and material properties to the polymers prepared therefrom, including particularly advantageous degradation profiles.

U.S. Pat. No. 5,099,060 discloses diphenolic monomers based on 3-(4-hydroxy-phenyl) propionic acid and L-tyrosine alkyl esters (desaminotyrosyl-tyrosine alkyl esters). Subsequent related patents involve variations of this basic monomer structure, including halogenated radiopaque diphenolic monomers, such as the 3,5-di-iododesaminotyrosyl-tyrosine esters ($I_2$DTR, wherein R is an alkyl group, e.g., E=ethyl, H=hexyl, O=octyl, etc.) disclosed by U.S. Patent Application Publication No. 20060034769. The disclosures of both publications are incorporated herein by reference. These monomers, although useful in many applications, have several limitations:

In the context of these teachings, the term "degradation" is defined as the process leading to the chemical cleavage of the polymer backbone, resulting in a reduction in polymer molecular weight and mechanical strength. The rate of polymer degradation under physiological conditions is predominantly determined by the type of bonds used to link the individual polymer repeat units together. Hence, polyanhydrides, e.g., polymers containing the highly labile anhydride linkage, will tend to degrade faster than polyesters. In contrast, the term "resorption" is defined as the process leading to a reduction of the mass of an implanted device. The rate of resorption is predominantly governed by the solubility of the polymer itself or its degradation products. The resorption of an implant is complete, once the entire mass of the implant has been removed from the implant site. Degradation and resorption do not always go hand-in-hand. Just for the purpose of providing an illustrative example, a sugar cube in water will "resorb" (e.g., lose mass and ultimately disappear) without any chemical degradation process. Likewise, comparing the degradation and resorption profiles of two different polyanhydrides, one can expect that both polymers will degrade when exposed to aqueous media, but the polymer degrading into more soluble degradation products will be losing mass faster and will, therefore, be the polymer that will resorb faster when implanted in a patient.

Use of monomers having two phenolic hydroxyl groups, as disclosed in the above mentioned Patent Applications, tend to limit the resulting homopolymers to fully aromatic backbone structures. Such polymers have generally good mechanical properties—but slow degradation rates. Moreover, when the monomers are sparingly soluble in water, the degradation products formed during polymer degradation are often also sparingly soluble in water. This property can slow or prevent the degrading polymer from being resorbed at a time scale that is concomitant with polymer degradation. Hence, such polymers will tend to have some use limitations as medical implant materials when the processes of degradation and resorption need to occur concomitantly. The previously described homopolymers prepared from the previously described sparingly-soluble monomers will not have any significant weight loss while the degradation of the homopolymer backbone results in reduction in the polymer molecular weight and loss of mechanical strength. As a result, implantable medical devices and drug delivery implants prepared from the previously described homopolymers that are intended to be resorbed are still substantially undissolved at the end of their useful life as measured by reduction in polymer molecular weight or mechanical strength.

This is particularly a problem for drug delivery implants and implantable medical devices that are intended to be replaced as part of a long-term treatment regimen. For example, a polymeric implant for the delivery of birth control hormones is intended to be replaced at the terminal stage of polymer degradation when essentially all of the hormones have been released as a consequence of polymer backbone degradation and mass loss. However, implants formed with many of the previously described homopolymers will not only be substantially undissolved when a replacement device must be implanted, significant mass will remain when the next replacement device is due for implantation. This creates the untenable situation where patient would be expected to endure having several depleted polymeric drug delivery implants in their body at various stages of resorption while replacement devices continue to be implanted at a periodic rate.

Homopolymers of non-aromatic amino acids have been prepared. Examples are polyglycine, polyalanine, polyserine, polyleucine. However, despite their apparent potential as biomaterials, such poly(amino acids) have actually found few practical applications. A major problem is that most of the poly(amino acids) are highly intractable (e.g., non-processable by conventional thermal or solvent fabrication methods), which limits their utility.

The elegant synthesis of a copolymer derived from lactic acid and lysine was reported by Barrera et al., Macromol., (28), 425-432 (1995). The lysine residue was utilized to chemically attach a cell-adhesion promoting peptide to the copolymer.

Other polymers of amino acids and hydroxy acids are disclosed by U.S. Pat. No. 3,773,737. The non-aromatic copolymers were random copolymers prepared from cyclic monomers by ring-opening polymerization. The composition of the copolymers is highly dependent on the relative reactivity of the two types of cyclic monomers and on the exact polymerization conditions used. It is hard to control the composition and hard to predict the polymer properties. Also, there may be large batch-to-batch variations in the polymer microstructure and sequence. Further, most previous reports only described polymers of relatively low molecular weight ($M_W<10,000$).

There are very few degradable polymers for medical uses that have been successfully commercialized. Poly(glycolic acid) (PGA), poly(lactic acid) (PLA) and their copolymers are representative examples. However, these polymers degrade to form tissue-irritating acids. Polymers of tyrosine and hydroxy acids such as glycolic acid and lactic acid have also been prepared and are disclosed by U.S. Pat. No. 6,284,862. There still remains a need for bioresorbable polymers suitable for use as tissue-compatible materials.

For example, many investigators in the emerging field of tissue engineering have proposed to engineer new tissues by transplanting isolated cell populations on biomaterial scaffolds to create functional new tissues in vivo. Bioresorbable materials whose degradation and resorption rates can be tailored to correspond to the rate of tissue growth are needed. It is desirable that libraries of many different materials be available so that the specific polymer properties can be optimally matched with the requirements of the specific application under development.

SUMMARY OF THE INVENTION

This need is met by preferred embodiments of the present invention. Embodiments of the present invention provide novel classes of aliphatic-aromatic monomers and bioresorbable polymers derived therefrom that hydrolytically degrade under physiological conditions. In preferred embodiments the monomers are dipeptides of tyrosine analogs and amino acids with substituent groups through which the monomers can be polymerized. Monomer solubility and the mechanical properties of the polymer can be varied by selection of the amino acid which is incorporated into the dipeptide monomer.

An embodiment therefore provides polymers that include one or more repeating units having the structure of Formula I and/or Formula Ia:

$$-X_1-Ar-R_1-\overset{X_2}{\overset{\|}{C}}-\overset{R_2}{\overset{|}{N}}-AA-X_3- \qquad (I)$$

(Ia)

for which the variables are defined as follows:

Ar is a phenyl ring that is unsubstituted or substituted with from one to four substituents independently selected from halogen atoms, halomethyl groups, halomethoxy groups, methyl, methoxy, thiomethyl, nitro, sulfoxide and sulfonyl;

$R_1$ is selected from a bond and saturated and unsaturated, substituted and unsubstituted alkyl, heteroalkyl, alkenyl and heteroalkenyl groups containing from one to 10 carbon atoms;

$X_1$, $X_2$ and $X_3$ are independently selected from O, S and $NR_3$;

$R_2$ is selected from hydrogen and alkyl groups containing from one to thirty carbon atoms bonded only to the Formula I nitrogen atom, and $R_{2a}$ is an alkylene group covalently bonded to both the Formula Ia nitrogen atom and AA to define a heterocyclic ring;

$R_3$ is selected from hydrogen and alkyl groups containing from one to thirty carbon atoms;

AA has a pendant $COOR_4$ group in which $R_4$ is selected from hydrogen, alkyl, hetero-alkyl and alkylaryl groups containing up to 30 carbon atoms and alkyl-terminated poly (alkylene oxide) groups of molecular weight 100 to 10,000; and AA and $X_3$ of Formula I are selected so that ($R_2$—HN-)AA-$X_3$H defines an $X_3$H-substituted amino acid, and AA and $X_3$ of Formula Ia are selected so that defines an $X_3$H— substituted amino acid. ($R_2$—HN-)AA-$X_3$H is optionally N-alkyl substituted.

According to one embodiment, $R_2$ and $R_3$ are independently selected from alkylene groups containing from one to six carbon atoms. According to another embodiment, the $R_4$ groups contain 18 carbon atoms or less.

Alkyl, heteroalkyl, alkenyl and heteroalkenyl groups are straight-chained or branched. The heteroalkyl and heteroalkenyl groups contain from one to eight heteroatoms. Heteroatoms are independently selected from O, S and N-methyl. Examples of alkyl-terminated poly(alkylene oxides) include methoxy-terminated poly(ethylene glycols) (PEG) of molecular weight 400 to 4,000, methoxy-terminated poly (propylene glycols) (PPG), and methoxy-terminated block copolymers of PEG and PPG.

Aromatic rings may be optionally substituted with from 1 to 4 of the identified groups as long as the substitution patterns are chemically feasible. Any combination of substituents containing more than two nitro groups is potentially explosive and expressly excluded from these teachings.

Polymers that include repeating units of Formula I and/or Formula Ia may be referred to herein as "polymers of Formula I and Formula Ia" or "Formula I and Ia polymers." Polymers of Formula I and Formula Ia include polymers containing either or both Formula I and Formula Ia repeating units. Other repeating units may be present, including repeating units derived from desaminotyrosyl-tyrosine monomers, including the monomers disclosed by U.S. Pat. No. 5,099,060.

The present invention more specifically provides Formula I and Formula Ia polymers wherein AA and $X_3$ are selected so that ($R_2$—HN-)AA-$X_3$H and represent an alpha-amino acid wherein ($R_2$—HN-)AA-$X_3$H is optionally N-alkyl substituted. In a more specific embodiment, the alpha amino acid is a naturally-occurring amino acid. Alpha-amino acids from which the polymers of the present invention may be prepared include, but are not limited to, cysteine, threonine, serine, lysine, thyronine, thyroxine, hydroxy-proline, mercapto-proline, hydroxy-leucine, mercapto-leucine, hydroxy-isoleucine, mercapto-isoleucine, hydroxy-tryptophan, mercapto-tryptophan, mercapto-alanine, mercapto-valine and mercapto-phenylalanine.

Included among the polymer embodiments of the Formula I and Formula Ia are four distinct polymer embodiments. According to the first polymer embodiment, AA and $X_3$ are selected so that the degradation products of polymers of Formula I and Formula Ia resorb more quickly under physiological conditions than comparable polymers of desaminotyrosyl-tyrosine alkyl esters and the polymers have intrinsic physical properties suitable for use in load-bearing medical implants such as vascular or coronary stents. One example of comparable polymers of desaminotyrosyl-tyrosine alkyl esters are polymers with structural similarities that provide essentially the same molecular weight.

For purposes of the present invention, "physiological conditions" are defined as storage in phosphate buffered saline solution (PBS), 0.1 M, pH 7.4 at 37° C., and polymers that resorb more quickly are defined as containing at least 10 mol % of monomers comprising either the Formula I or Formula Ia repeating units having a PBS solubility under physiological conditions of at least about 3 mg/mL, e.g., preferably, at least about 5 mg/mL, to provide the desired rate of resorption. The monomer comprising either Formula I or Formula Ia repeating units may contain other moieties or substituents, provided that the requisite degree of PBS solubility is conserved. All of this is readily determined by one of ordinary skill in the art without undue experimentation. Embodiments according to the present invention include polymers containing up 90 mol % of said monomer, and polymers consisting entirely of said monomers. Other monomers and repeating units may be used to design polymers with a desirable rate of resorption.

"Load-bearing medical implants" are defined as implantable medical devices that are required by their intended use to withstand forces caused by compression, bending, or stretching of the implant. Because of the significant variations in shape, size, and use of load-bearing medical implants, the physicomechanical properties of polymers suitable for load-bearing implants cannot be described in precise terms, except for the following requirements: As a general rule, load-bearing medical implants can only be fabricated from (i) amorphous polymers having glass transition temperatures greater than 37° C. when fully hydrated under physiological conditions and (ii) from crystalline or partially crystalline polymers that have a crystalline melting temperature greater than 37° C. when fully hydrated under physiological conditions. In addition, the equilibrium water content when fully hydrated under physiological conditions is typically less than 20 wt %, preferably less than 10 wt % and more preferably less than 5 wt %. These required polymer properties can be achieved by carefully optimizing the chemical composition of the polymer backbone structure, including Formula I repeating units, Formula Ia repeating units, other repeating units, and combinations thereof.

Examples of Formula I and Formula Ia polymers according to the first polymer embodi-ment include, but are not limited to, polymers in which AA and $X_3$ of Formula I are selected so that ($R_2$—HN-)AA-$X_3$H defines the amino acid cysteine, and AA and $X_3$ of Formula Ia are selected so that:

defines an amino acid selected from cis-hydroxy-proline, trans-hydroxy-proline, cis-mercapto-proline and trans-mercapto-proline.

According to the second polymer embodiment of the invention, AA and $X_3$ are selected so that the degradation products of the polymers of Formula I and Formula Ia do not necessarily resorb significantly more quickly under physiological conditions than comparable polymers of desamino-tyrosyl-tyrosine alkyl esters. That is, they resorb at about the same rate or slower. However, polymers according to this embodiment still have intrinsic physical properties suitable for use in load-bearing medical implants.

Polymers according to this embodiment are defined as containing at least 10 mol % of monomers comprising either Formula I or Formula Ia repeating units having a PBS solubility under physiological conditions of less than about 3 mg/mL to provide the desired slow rate of resorption, and having the requisite glass transition or crystalline melting temperature and equilibrium water content for the desired load-bearing intrinsic physical properties. The solubility may be as low as 0.01 mg/mL. Examples of polymers according to the second polymer embodiment include, but are not limited to, polymers in which AA and $X_3$ of Formula I are selected so ($R_2$—HN-)AA-$X_3$H defines an amino acid selected from mercaptophenylalanine, 5-hydroxytryptophan, thryronine and thyroxine.

According to the third polymer embodiment of the invention, AA and $X_3$ are selected so that the degradation products of the polymers of Formula I and Formula Ia do not necessarily resorb significantly more quickly under physiological conditions than comparable polymers of desaminotyrosyl-tyrosine alkyl esters and the polymers do not have intrinsic physical properties suitable for use in load-bearing medical implants. Polymers according to this embodiment have utility in other uses for biocompatible polymers, such as drug delivery implants, bridging materials, tissue sealants, adhesion prevention materials, tissue scaffolds where rigidity is not essential, and the like.

Polymers lacking intrinsic physical properties suitable for use in load-bearing medical implants include, if the polymer is amorphous, a glass transition temperature less than 37° C. when fully hydrated under physiological conditions and, if the polymer is crystalline, a crystal-line melting temperature less than 37° C. when fully hydrated under physiological conditions. In addition, the equilibrium water content when fully hydrated under physiological conditions is typically greater than 20 wt %.

Polymers according to this embodiment are defined as being polymerized from at least 10 mol % of monomers that comprising either Formula I or Formula Ia repeating units having a PBS solubility under physiological conditions effective to provide the desired slower rate of resorption, and have the requisite glass transition or crystalline melting temperature and equilibrium water content for the desired intrinsic physical properties. That is, the monomers have a PBS solubility under physiological conditions of less than about 3 mg/mL, wherein the solubility may be as low as 0.01 mg/mL. Polymers according to this embodiment of the invention include, but are not limited to, polymers in which AA and $X_3$ of Formula I are selected so that ($R_2$—HN-)AA-$X_3$H defines an amino acid selected from hydroxy-leucine, mercapto-leucine, hydroxy-isoleucine, mercapto-isoleucine and mercapto-valine.

According to the fourth polymer embodiment of the invention, AA and $X_3$ are selected so that the degradation products of polymers of Formula I and Formula Ia resorb more quickly under physiological conditions than comparable polymers of desamino-tyrosyl-tyrosine alkyl esters and the polymers do not have intrinsic physical properties suitable for use in load-hearing medical implants. Polymers according to this embodiment are defined as being polymerized from at least 10 mol % of monomers comprising either Formula I or Formula Ia repeating units having a PBS solubility under physiological conditions to provide the desired rate of resorption, and having the requisite glass transition or crystalline melting temperature and equilibrium water content for the desired intrinsic physical properties. Examples of polymers according to this embodiment of the invention include, but are not limited to, polymers in which AA and $X_3$ of Formula I are selected so ($R_2$—HN-)AA-$X_3$H defines an amino acid selected from cysteine and serine.

Independent of each polymer embodiment, the same Formula I and/or Formula Ia repeating units can provide both the desired resorption properties and the intrinsic physical properties. In the alternative, one set of Formula I and/or Formula Ia repeating units are selected to provide the desired rate of resorption and combined with a second set of Formula I and/or Formula Ia repeating units selected to provide intrinsic physical properties. Additional repeating units can be present that also contribute to the desired degradation properties and intrinsic physical properties, such as repeating units with pendant free carboxylic acid groups, including repeating units of Formula I and Formula Ia with pendant free carboxylic acid groups. The selection of appropriate repeating units for each polymer embodiment is readily determined by one of ordinary skill in the art without undue experimentation.

Independent of each polymer embodiment, the present invention provides polymers according to Formula I and Formula Ia in which $X_1$ and $X_2$ are O, wherein the polymers are prepared from monomers that are formed from the reaction products of a hydroxy-phenylalkanoic or alkenoic acid and an amino acid. $R_1$ is preferably ethylene so that the phenylalkanoic acid is desaminotyrosine (DAT), also referred to as 4-hydroxy-phenylpropanoic acid. When $X_1$ and $X_2$ are O and $R_1$ is ethylene, the Formula I and Formula Ia polymers are referred to as "DAT derivatives."

More specifically, Formula I and Formula Ia polymers are provided independent of each embodiment that are formed from monomers that are amide, thioamide or imide reaction products of phenylalkanoic acid, preferably DAT, and amino acid starting materials, with modification as needed. DAT and the phenylalkanoic acid analogs thereof unexpectedly contribute useful physical properties to the Formula I and Ia polymers that are not obtained from polymers formed from monomers combining two or more amino acids. Therefore, "phenyl-alkanoic acid analogs of DAT" are defined as compounds contributing at least one advantageous physical property to the Formula I and Ia polymers that are also obtained with Formula I and Ia polymers that are DAT derivatives. For purposes of the present invention, a "derivative" of a compound is defined as the product of a reaction in which the compound is a reactant. Thus, a "DAT derivative" is a compound produced by reacting DAT with a co-reactant, etc.

The advantageous physical properties in no particular order of importance include DAT's lack of a chiral center, so that DAT, unlike amino acids, does not give rise to diastereomers when coupled with amino acids. Also, because the COOH on DAT is not linked to a chiral carbon, there is no racemization during coupling to make the monomer. Furthermore, DAT is easier to iodinate than an aromatic amino acid such as tyrosine when a radio-opaque polymer is desired. In addition, despite not being a nutrient, DAT is naturally found in the body as an end-stage metabolite and is excreted in urine. As a natural constituent of human metabolism, DAT has low toxicity, attributable in part to being a closely-related analog of the essential amino acid L-tyrosine. More significantly, DAT is an end stage metabolite; there is no cause for concern that DAT may be further converted to other metabolites. In addition to being non-toxic, DAT's aromatic ring imparts good mechanical properties to polymers, and removal of the tyrosine amino group gives better polymer processing properties compared to amino acids.

The present invention also provides independent of any polymer embodiment, co-polymers having two different repeating units with the structure of Formula I or Formula Ia, wherein the copolymer has a first repeating unit in which $R_4$ is hydrogen, so that $COOR_4$ is a pendant free carboxylic acid group, and a second repeating unit in which $R_4$ is an alkyl group containing up to 30 carbon atoms, so that $COOR_4$ is a pendant alkyl ester group. Among the copolymers provided are copolymers in which between about 1 and about 50% of the AA groups have pendant free carboxylic acid groups. Among other copolymers provided are copolymers in which greater than about 5% but less than about 33% of the AA groups have pendant free carboxylic acid groups. According to one embodiment $R_4$ is an alkyl group containing less than 18 carbon atoms This is not to say that polymer embodiments according to the present invention do not include polymers having Formula I or Formula Ia repeating units with pendant free carboxylic acid groups. Monomers comprising Formula I or Formula Ia repeating units with pendant free carboxylic acid groups have increased solubility in PBS under physiological conditions than their ester counterparts. Thus, one determining factor for whether a polymer according to the present invention falls within the first polymer embodiment or the second polymer embodiment is the molar fraction of repeating units with pendant free carboxylic acid groups. This is also one determining factor for whether a polymer according to the present invention falls within the third polymer embodiment or the fourth polymer embodiment. Furthermore, the solubility of a particular monomer can be modulated to less solubility in PBS by variation in the chain length of $R_3$ and $R_4$. This is independent of the effect of these groups on the load bearing capacity of the subsequent polymer, e.g., long side chains will lower solubility and may or may not affect wet Tg and/or Tm.

Thus, a highly esterified or fully esterified version of a polymer according to the present invention may fall within the second or third polymer embodiment, while a less esterified counterpart with more pendant free carboxylic acid groups may fall within the first or fourth polymer embodiment. Stated another way, one of ordinary skill in the art can design or modify a polymer to have a molar fraction of monomeric repeating units with pendant free carboxylic acid groups so that the polymer falls within the first polymer embodiment rather than the second polymer embodiment, or within the fourth polymer embodiment rather than the third polymer embodiment.

Furthermore, polymers according to the present invention with pendant free carboxylic acid groups have higher glass transition temperatures or crystalline melting temperatures than their unsubstituted counterparts. Thus, polymers with higher molar fractions of monomeric repeating units with pendant fee carboxylic acid groups tend to fall within the first polymer embodiment.

Polymers with a sufficient number of aromatic rings sufficiently substituted with bromine or iodine are inherently radio-opaque. The present invention therefore also provides, independent of any particular polymer embodiment, polymers according to Formula I and Ia in which the aromatic rings are substituted with at least one iodine or bromine atom, on at least one and preferably on both ring positions ortho to $X_1$. In a more specific aspect of each embodiment, at least 50% of the Ar groups are substituted with from two to four iodine atoms, bromine atoms, or combinations thereof.

This is not to say that polymer embodiments according to the present invention do not include polymers having Formula I or Formula Ia repeating units in which the aromatic rings are bromine- or iodine-substituted. Polymers comprising Formula I or Formula Ia repeating units with bromine- or iodine-substituted aromatic rings have higher glass transition temperatures or crystalline melting temperatures than their unsubstituted counterparts. Thus, another determining factor for whether a polymer according to the present invention falls within the first polymer embodiment or the second polymer embodiment is the molar fraction of repeating units with bromine or iodine substituted aromatic rings. This is also another determining factor for whether a polymer according to the present invention falls within the third polymer embodiment or the fourth polymer embodiment.

Thus, a highly bromine or iodine ring-substituted version of a polymer according to the present invention may fall within the first or second polymer embodiment, while a less substituted counterpart may fall within the third or fourth polymer embodiment. Stated another way, one of ordinary skill in the art can design or modify some polymers to fall within the first or second embodiment rather than the third or fourth embodiment by increasing the level of bromine or iodine ring substitution. While not every polymer according to the present invention can be moved between the first and fourth polymer embodiments or the second and third polymer embodiments by adjusting or selecting the degree of iodine or bromine ring-substitution, one of ordinary skill in the art will readily recognize the polymers that can be modified or designed in this manner. Furthermore it is important to note that the level of bromine or iodine substitution may not be subject to modification if it is necessary for the polymer to be radio-opaque or radio-transparent.

In terms of the prior art, the new polymers of the present invention, including the polymers of all four polymer embodiments, are similar to the desaminotyrosyl-tyrosine alkyl ester polymers disclosed in U.S. Pat. No. 5,099,060. An important difference is that the tyrosine alkyl ester unit has been replaced by another amino acid ester selected for its contribution to the resorbability of the polymeric implant, or for its contribution to the intrinsic physical properties of the polymer related to suitability for use in load bearing medical implants, or both.

The present invention is thus based in part on the recognition that valuable polymers are obtained when DAT and its analogs are kept constant and the monomer and polymer properties are modified by varying the amino acid coupled to the DAT or DAT analog that otherwise would not be obtained if at the same time the DAT or DAT analog was replaced by amino acids or other amino acid analogs. The new monomers, the resulting polymers, and their respective properties represent new and valuable biomaterials in addition to the desamino-tyrosyl-tyrosine alkyl ester monomers and the polymers polymerized therefrom disclosed before.

New polymers are formed from DAT—amino acid monomers in the same fashion as the desaminotyrosyl-tyrosine alkyl ester—derived polymers disclosed before. In particular, polymers according to the present invention include polycarbonates, polyesters, polyphosphazines, polyphosphoesters and polyiminocarbonates, having the structure of Formula II and IIa:

wherein $X_1$, $X_2$, $X_3$, Ar, $R_1$, $R_2$, $R_{2a}$, AA, and the embodiments thereof, are the same as described above with respect to Formula I and Formula Ia and A is selected from:

wherein $R^{10}$ is selected from H, saturated and unsaturated, substituted and unsubstituted alkyl, heteroalkyl, alkenyl and heteroalkenyl groups containing from one to 18 carbon atoms, and $R^{12}$ is selected from saturated and unsaturated, substituted and unsubstituted alkyl, heteroalkyl, alkenyl and heteroalkenyl groups containing from one to 18 carbon atoms and alkylaryl, hetero-alkylaryl, alkenylaryl and heteroalkenylary groups containing from three to 12 carbon atoms.

Polymers according to the present invention include polyethers, polyurethanes, polycarbamates, polythiocarbonates, polycarbonodithionates and polythiocarbamates. Polycarbonates, specifically poly(amide carbonates), as well as polyurethanes, polycarbamates, polythiocarbonates, polycarbonodithionates and polythiocarbamates are prepared by the process disclosed by U.S. Pat. No. 5,198,507, the disclosure of which is incorporated by reference. Polyesters, specifically poly(ester amides), are prepared by the process disclosed by U.S. Pat. No. 5,216,115, the disclosure of which is incorporated herein by reference. Polyiminocarbonates are prepared by the process disclosed by U.S. Pat. No. 4,980,449, the disclosure of which is incorporated by reference. Polyethers are prepared by the process disclosed by U.S. Pat. No. 6,602, 497, the disclosure of which is incorporated by reference.

Independent of any particular polymer embodiment, the present invention also provides polymers that include a recurring unit according to Formula I, Formula Ia, Formula II and/or Formula IIa that are copolymerized with any number of other recurring units. For example the present invention provides polymers having a recurring unit according to Formula I, Formula Ia, Formula II and/or Formula IIa that are block co-polymerized with recurring polyalkylene oxide block units having a structure according to Formula III:

$$-\!\!+\!\!B-\!\!A^2\!\!+\!\!- \quad (\text{III})$$

wherein B is $-\!O\!-\!((CHR^6)_p\!-\!O)_q\!-\!$; each $R^6$ is independently H or $C_1$ to $C_3$ alkyl; p is an integer ranging between about one and about 4; q is an integer ranging between about one and about 100; and $A^2$ is the same as A in Formula II and IIa. Block copolymers according to the present invention include copolymers containing molar fractions of alkylene oxide between about 0.1 and about 25%. Other block copolymers according to the present invention contain molar fractions of alkylene oxide between about 0.5 and about 10%. Yet other block copolymers according to the present invention contain molar fractions of alkylene oxide between about 1 and about 5%.

This is not to say that polymer embodiments according to the present invention do not include polymers that are poly (alkylene oxide) block copolymers. Polymers that are block-copolymerized with poly(alkylene oxides) tend to have lower glass transition temperatures or crystalline melting temperatures than their counterparts without poly(alkylene oxide) blocks. Thus, another determining factor for whether a polymer according to the present invention falls within the first polymer embodiment or the second polymer embodiment instead of the third polymer embodiment or the fourth polymer embodiment is whether the polymer is block copolymerized with poly(alkylene oxide) and molar fraction of poly(alkylene oxide) blocks.

Thus, a poly(alkylene oxide) block copolymer may fall within the third or fourth polymer embodiment, while a counterpart polymer with a lesser degree of block copolymerization, or one that is free of poly(alkylene oxide) blocks may fall within the first or second polymer embodiment, while a less substituted counterpart may fall within the third or fourth polymer embodiment. Stated another way, one of ordinary skill in the art can design or modify some polymers to fall within the first or second embodiment rather than the third or fourth embodiment by decreasing or eliminating poly(alkylene oxide) block copolymerization.

Independent of any particular polymer embodiment, the present invention also provides copolymers with two different repeating units with the structure of Formula I and/or Formula II, wherein the copolymer has a first repeating unit in which $R_2$ is hydrogen, and a second repeating unit in which $R_2$ is an alkyl group containing from one to thirty carbon atoms. Copolymers with repeating units in which $R_2$ is alkyl are referred to as N-substituted copolymers and are prepared from N-substituted monomers by the methods disclosed by U.S. patent application Ser. No. 11/873,979, the disclosure of which is incorporated herein by reference. In one embodiment, $R_4$ is an alkyl group containing from one to six carbon atoms This is not to say that polymer embodiments according to the present invention do not include polymers having N-substituted Formula I or Formula Ia repeating units. Polymers comprising N-substituted Formula I or Formula Ia repeating units tend to have lower glass transition temperatures or crystalline melting temperatures than their unsubstituted counterparts. Thus, another determining factor for whether a polymer according to the present invention falls within the first polymer embodiment or the second polymer embodiment is the molar fraction of N-substituted repeating units. This is also another determining factor for whether a polymer according to the present invention falls within the third polymer embodiment or the fourth polymer embodiment.

Thus, a highly N-substituted version of a polymer according to the present invention may fall within the third or fourth polymer embodiment, while a less substituted counter-part with may fall within the first or second polymer embodiment. Stated another way, one of ordinary skill in the art can design or modify some polymers to fall within the first or second embodiment rather than the third or fourth embodiment by decreasing the level of N-substitution. This can be done in combination with increasing the level of bromine or iodine ring substitution. While not every polymer according to the present invention can be moved between the first and fourth polymer embodiments or the second and third polymer embodiments by adjusting or selecting the degree of N-substitution, alone or in combination with adjusting or selecting the level of iodine or bromine ring-substitution and degree of poly(alkylene oxide) block copolymerization, one of ordinary skill in the art will readily recognize the polymers that can be modified or designed in this manner.

N-substituted copolymers according to the present invention include copolymers in which the molar fraction of N-substituted monomer is between about 1 and about 90%. N-substituted copolymers according to the present invention also include copolymers with a molar fraction of N-substituted monomer between about 5 and about 25%. Yet other N-substituted co-polymers according to the present invention include copolymers with a molar fraction of N-substituted monomer between about 7.5 and about 12.5%.

According to another aspect of the present invention, monomer compounds are provided having the structure of Formula IV and Formula IVa:

for which the variables are defined as follows:

Ar is a phenyl ring that is unsubstituted or substituted with from one to four substituents independently selected from the group consisting of halogen atoms, halo-methyl groups, halomethoxy groups, methyl, methoxy, thiomethyl, nitro, sulfoxide and sulfonyl;

$R_1$ is selected from a bond and saturated and unsaturated, substituted and unsubstituted alkyl, heteroalkyl, alkenyl and heteroalkenyl groups containing from one to 12 carbon atoms;

$X_1$, $X_2$ and $X_3$ are independently selected from the group consisting of O, S and $NR_3$;

$R_2$ is selected from the group consisting of hydrogen and alkyl groups containing from one to thirty carbon atoms bonded only to N, or $R_{2a}$ is an alkylene group covalently bonded to both the nitrogen atom and AA, so that —N—$R_{2a}$-AA- define a heterocyclic ring;

$R_3$ is selected from the group consisting of hydrogen and alkyl groups containing from one to thirty carbon atoms;

AA has a pendant $COOR_4$ group in which $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000; and AA and $X_3H$ of Formula IV are selected so that ($R_2$—HN-)AA-$X_3H$ define an amino acid and AA and $X_3H$ of Formula IVa are selected so that define an $X_3H$-substituted amino acid. According to one embodiment:

defines a proline ring.

According to one embodiment, $R_2$ and $R_3$ are independently selected from alkylene groups containing from one to six carbon atoms. According to another embodiment, the $R_4$ groups contain 18 carbon atoms or less.

Independent of any particular polymer embodiment, polymers according to the present invention include polymers in which the thermal decomposition temperature is greater than the glass transition temperature or the crystalline melt temperature. Such polymers can be melt-processed and can be shaped into different three-dimensional structures for specific uses by conventional polymer-forming techniques such as extrusion and injection molding. The solvent-casting and compression molding techniques described in earlier patents disclosing polymers polymerized from tyrosine-derived diphenol compounds can also be used for all polymers provided by the present invention, regardless of whether they can be melt-processed.

Therefore, according to another aspect of the present invention, blood-contacting or tissue-implantable medical devices are provided, formed from the polymers of the present invention. Preferably, the devices are formed by thermal fabrication. Such devices include hernia repair devices. Load-bearing medical devices are formed from the first and second polymer embodiments, while medical devices that are not load-hearing may be formed from all four polymer embodiments.

Load-bearing medical devices formed from the first and second polymer embodiments of the present invention include stents for the treatment of a body lumen including, but not limited to, any blood vessels, the esophagus, urinary tract, bile tract, and the ventricles of the central nervous system (brain and spinal cord). Preferred stents are formed from or coated with radio-opaque polymers according to the first and second polymer embodiments of the present invention, so that fluoroscopic imaging can be used to guide positioning of the device. One radio-opaque, bioresorbable stent provided by the present invention is formed from a bioresorbable polymer with sufficient halogen atoms to render the stent inherently visible by X-ray fluoroscopy during stent placement.

Included among the medical devices formed from the polymers of the present invention are embolotherapy products. Embolotherapy products provided by the present invention include particulate formulations of biocompatible, bioresorbable polymers according to all four polymer embodiments of the present invention. Among the embolotherapy products provided by the present invention are embolotherapy products formed from the radio-opaque polymers provided by the present invention that contain a sufficient number of halogen atoms to render the embolotherapy product inherently radio-opaque.

Another specific application for which polymers provided by the present invention are particularly useful is the fabrication of scaffolds for tissue engineering on which isolated cell populations are transplanted to engineer new tissues. The polymers are formed into porous devices as described by Mikos et al., Biomaterials, 14, 323-329 (1993) or Schugens et al., J. Bio-med. Mater. Res., 30, 449-462 (1996) or U.S. Pat. No. 6,103,255 to allow for the attachment and growth of cells as described in Bulletin of the Material Research Society, Special Issue on Tissue Engineering (Guest Ed.: Joachim Kohn), 21(11), 22-26 (1996). Thus the present invention also provides tissue scaffolds having a porous structure for the attachment and proliferation of cells either in vitro or in vivo formed from polymers provided by the present invention. Which polymer embodiment disclosed herein should be used to fabricate the scaffold will depend upon the degree of rigidity and rate of resorption required by the intended scaffold use.

Another specific application for which polymers provided by the present invention may be used is the fabrication of implantable drug delivery devices where a pharmaceutically active moiety is admixed within the polymeric matrix for slow release, including devices for ophthalmic drug delivery. The polymers provided by the present invention are combined with a quantity of a biologically or pharmaceutically active compound sufficient to be therapeutically effective as a site-specific or systemic drug delivery system as described by Gutowska et al., J. Biomater. Res., 29, 811-21 (1995) and Hoffman, J. Contr. Rel., 6, 297-305 (1987). Accordingly, the present invention also provides a method for site-specific or systemic drug delivery by implanting in the body of a patient in need thereof an implantable drug delivery device containing a therapeutically effective amount of a biologically or a physiologically active compound (e.g., a drug) in combination with a polymer provided by the present invention.

Independent of any particular polymer embodiment, the polymers provided by the present invention have good film-forming properties. An important phenomena observed for the polymers provided by the present invention having poly (alkylene oxide) block copolymer segments is the temperature dependent phase transition of the polymer gel or the polymer solution in aqueous solvents. As the temperature increases, the gel of the polymers undergo a phase transition to a collapsed state, while polymer solutions precipitate at a certain temperature or within certain temperature ranges. The polymers of the present invention having poly(alkylene oxide) segments, and especially those that undergo a phase transition at about 30 to 40° C. on heating can be used as biomaterials for drug release and clinical implantation materials. Specific applications include films and sheets for the prevention of adhesion and tissue reconstruction, as well as injectable drug delivery systems that exist as a solution at room temperature and that precipitate to form a solid drug release device upon injection into the patient.

Therefore, the present invention also provides sheets or coatings for application to exposed or injured tissues for use as barrier for the prevention of surgical adhesions as described by Urry et al., Mat. Res. Soc. Symp. Proc., 292, 253-64 (1993), which are formed from the poly(alkylene oxide) block copolymers provided by the present invention. In addition, the present invention also provides a method for preventing the formation of adhesions between injured tissues by inserting as a barrier between the injured tissues a sheet or a coating of the poly(alkylene oxide) block copolymers provided by the present invention.

The poly(alkylene oxide) segments decrease the surface adhesion of the polymers provided by the present invention. As the molar fraction of poly(alkylene oxide) increases, the surface adhesion decreases. Coatings containing polymers with poly(alkylene oxide) segments provided by the present invention may thus be prepared that are resistant to cell attachment and are useful as non-thrombogenic coatings on surfaces in contact with blood. Such polymers also resist bacterial adhesion in this and in other medical applications as well. The present invention therefore also provides blood contacting devices and medical implants having surfaces coated with the poly(alkylene oxide) block copolymers provided by the present invention.

The coated surfaces are preferably polymeric surfaces. Methods provided by the present invention therefore further include implanting in the body of a patient a blood-contacting device or medical implant having a surface coated with a polymer provided by the present invention containing poly (alkylene oxide) block copolymer segments.

By varying the molar fraction of poly(alkylene oxide) segments in the block copolymers provided by the present invention, the hydrophilic/hydrophobic ratios of the polymers can be attenuated to adjust the ability of the polymer coatings to modify cellular behavior. Increasing levels of poly(alkylene oxide) inhibit cellular attachment, migration and proliferation, while increasing the amount of pendent free carboxylic acid groups promotes cellular attachment, migration and proliferation. The present invention therefore also provides methods for regulating cellular attachment, migration and proliferation by contacting living cells, tissues, or biological fluids containing living cells with the polymers provided by the present invention.

Through pendant free carboxylic acid groups, derivatives of biologically and pharmaceutically active compounds, including drugs, can be attached to the polymer backbone by covalent bonds linked to the carboxylic acid pendent chain. This provides for the sustained release of the biologically or pharmaceutically active compound by means of hydrolysis of the covalent bond between the drug and the polymer backbone. The present invention therefore also provides polymers according to the depicted formulas in which $R_4$ is a biologically or pharmaceutically active compound covalently attached to the polymer backbone.

Other features of the present invention will be pointed out in the following description and claims, which disclose the principles of the invention and the best modes which are presently contemplated for carrying them out.

DETAILED DESCRIPTION OF PREFERRED EMBODIMENTS

The present invention introduces a novel class of monomers and copolymers polymerized therefrom in which an amino acid and an amino acid derivative are coupled together to form the new monomers depicted in formula IV and formula IVa:

$X_1$, $X_2$, $X_3$, Ar, $R_1$, $R_2$, $R_{2a}$, AA and the embodiments thereof are the same as described above with respect to Formula I and Formula Ia. The new monomers are then polymerized to form the new, useful polymers depicted in Formula I, Formula Ia, Formula II and Formula IIa. The Formula IV and Formula IVa monomers are prepared following standard procedures of peptide chemistry such as disclosed in J. P. Greenstein and M. Winitz, Chemistry of the Amino Acids, (John Wiley & Sons, New York 1961) and Bodanszky, Practice of Peptide Synthesis (Springer-Verlag, New York, 1984).

Specifically, the monomers are prepared by coupling an aromatic compound having the structure of formula V:

with an amino acid having the structure of Formula VIa or Formula VIb:

More specifically, the two compounds are coupled by means of carbodiimide-mediated coupling reactions in the presence of hydroxybenzotriazole according to the procedure disclosed in U.S. Pat. Nos. 5,587,507 and 5,670,602, the disclosures of both of which are hereby incorporated by reference. Suitable carbodiimides are disclosed therein. The preferred carbodi-imide is 1-ethyl-3-(3-dimethylaminopropyl) carbodiimide hydrochloride (EDCI.HCl). The crude monomers can be recrystallized twice, first from 50% acetic acid and water and then from a 20:20:1 ratio of ethyl acetate, hexane and methanol, or, alternatively, flash chromatography on silica gel is used, employing a 100:2 mixture of methylene chloride:methanol as the mobile phase.

Monomers according to one embodiment of the present invention have a molecular weight less than 1000. According to another embodiment the monomer molecular weight is less than 500.

Figure 1:
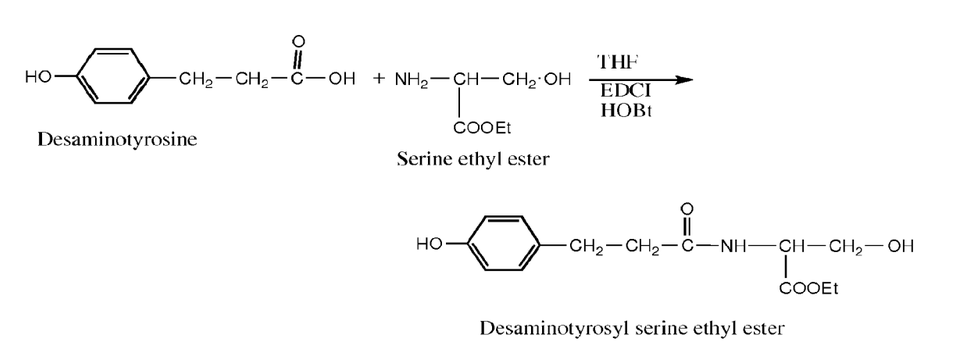
FIG. 1 depicts a method according to the present invention in which desaminotyrosyl tyrosine is coupled with serine ethyl ester using a carbodiimide coupling agent.

Using the reaction coupling desaminotyrosine and serine as an example, a schematic view of the synthetic route is shown in FIG. 1.

Desaminotyrosine and serine are but two examples of suitable reactants. The other Formula V aromatic compounds and the other Formula VIa and Formula VIb amino acids can be substituted for desaminotyrosine and serine, respectively, in the depicted reaction scheme.

According to one embodiment, $X_1$, $X_2$ and $R_1$ are selected so that Formula V defines a hydroxy-phenylalkanoic or alkenoic acid. Examples of Formula V acids include 4-hydroxycinnamic acid, 4-hydroxy-benzoic acid, 4-hydroxy-phenylethanoic acid, 4-hydroxy-phenyl-propanoic acid (DAT), 4-hydroxy-phenylbutanoic acid and the like.

According to another embodiment, $R_2$, $R_{2a}$, AA and $X_3$ are selected so that Formula VIa and Formula VIb define an alpha-amino acid. The Formula VIa alpha-amino acid is optionally N-alkyl substituted. In a more specific embodiment, the alpha amino acid is a naturally-occurring amino acid. In an even more specific embodiment, the alpha amino acid is an essential amino acid. Even more specifically, $R_2$, AA and $X_3$ may be selected to define an amino acid selected from cysteine, threonine, serine, lysine, thyronine, thyroxine, hydroxy-proline, mercapto-proline, hydroxy-leucine, mercapto-leucine, hydroxy-isoleucine, mercapto-isoleucine, hydroxy-tryptophan, mercapto-tryptophan, mercapto-alanine, mercapto-valine and mercapto-phenylalanine.

According to another embodiment, the monomer of Formula IV or Formula IVa is an amide dimer of a hydroxyphenyl alkanoic or alkenoic acid and an amino acid. Specific examples of this embodiment of Formula IV and IVa monomers include desaminotyrosyl-serine, 3,5-diiododesaminotyrosyl-thyroxine, desaminotyrosyl-cysteine, desamino-tyrosyl-hydroxyproline and the like.

For purposes of the present invention, a "combination of variables" refers to the combin-ation of $X_1$, $X_2$, $X_3$, $R_1$, $R_2$, $R_{2a}$, $R_4$ and AA variables in Formula I, Formula Ia, Formula II, Formula IIa, Formula IV, Formula IVa, Formula V, Formula VIa and Formula VIb. The present invention provides polymers with combinations of variables and degrees of poly (alkylene oxide) block copolymerization that possess degradation product solubility and the intrinsic physical polymer properties related to suitability for use in load-bearing and non-load-bearing medical implants within one of the four polymer embodiments disclosed herein.

The combination of variables that achieve this result can be readily determined without undue experimentation by one of ordinary skill art guided by the present specification with the objective of achieving a polymer with one of the four combinations of degradation product solubility and intrinsic physical polymer properties described herein. Once appropriate variable combinations are selected, the synthesis of monomers and the polymerization of monomers into polymers is essentially conventional. Thioamide monomers ($X_2$=S) can be prepared using the method described by A. Kjaer (Acta Chemica Scandinavica, 6, 1374-83 (1952)). The amide group in the monomers or polymers can also be converted to thioamide groups using the fluorous analog of the Lawesson's reagent ($f_6LR$) described by Kaleta, et al., Org. Lett., 8(8), 1625-1628 (2006). The second method is preferable, since it allows the formation of the monomer first then allows the conversion of the amide group to the thioamide group. The present invention also includes polymers in which other carboxyl groups, such as the $COOR_4$ group, are replaced with thio groups.

For the conversion of the tyrosine derived amide monomers to the corresponding thioamides, the phenolic groups of the monomers are first protected by converting them to the diacetyl esters as shown in the above-referenced U.S. application Ser. No. 11/873,979 by treating the monomer with $Ac_2O$/pyridine. The protected monomer is then reacted with $f_6LR$ followed by base hydrolysis to the thioamide The transformation can also be carried out on the polymer using a similar procedure.

The N-substituted monomers and polymers of the present invention ($R_2$=one to thirty carbon atom alkyl) can be prepared by substituting commercially-available N-substituted starting materials for the starting materials of monomers containing unsubstituted amide groups, or by substituting monomers containing amide groups using non-N-substituted starting materials. Such conversions are described in the above-referenced U.S. patent application Ser. No. 11/873,979, which discloses in one embodiment the preparation of N-substituted alpha-amino acid com-pounds of Formula IVb from alanine, cysteine, glycine, histidine, isoleucine, phenylalanine, serine, threonine, tryptophan, tyrosine and valine that are subsequently coupled to 4-hydroxy-phenylalkanoic acids to provide N-substituted monomers having the structure of formula IV. According to a disclosed embodiment, $R_2$ contains from one to six carbon atoms.

Because the DAT and DAT analogs are non-chiral, unless otherwise indicated the products of this invention are R,S enantiomers. Preferably, however, when a chiral product is desired, the chiral product corresponds to the L-amino acid derivative. Alternatively, chiral products can be obtained via purification techniques which separates enantiomers from an R,S mixture to provide for one or the other stereoisomer. Such techniques are well known in the art.

Polymers according to the present invention may contain a plurality of repeating units containing an N-substituted amide group, wherein the N-substituents and degree of N-substitution are effective to render the polymer processable by a desired processing method. Preferably, the minimum degree of N-substitution is used. This can range from one to three mole percent to render a non-soluble polymer soluble in a given solvent to up to about 25 mole percent to make the same polymer thermally processable, for example, injection moldable. This can be readily determined by one of ordinary skill in the art without undue experimentation. N-methyl substituents are preferred. In certain circumstances, the degree of N-substitution may also be selected to determine whether the polymer falls within the first or second polymer embodiment rather than the third or fourth polymer embodiment.

The monomer compounds are polymerized to form bioerodable polymers for medical uses. The monomers can be used in any conventional polymerization process using the monomer —$X_1H$ and —$X_3H$ groups, including those processes that synthesize polymers traditionally considered hydrolytically stable and non-biodegradable. This includes polyesters, poly-carbonates, polyiminocarbonates, polyarylates, polyurethanes, poly(urethane carbonates), polyphosphazines, polyphosphoesters, polyethers, polycarbamates, polycarbonodithionates, polythiocarbonates and polythiocarbamates, as well as random block copolymers of these polymers with poly(alkylene oxides) as described in U.S. Pat. No. 5,658,995, the disclosure of which is incorporated herein by reference.

It is also understood that in the presentation of the various polymer formulae that the polymer structures represented may include homopolymers and heteropolymers, which include stereoisomers. Homopolymer is used herein to designate a polymer comprised of all the same type of monomers. Heteropolymer is used herein to designate a polymer comprised of two or more different types of monomer, which is also called a copolymer. A heteropolymer or co-polymer may be of kinds known as block, random and alternating. Further, with respect to the presentation of the various polymer formulae, products according to embodiments of the present invention may be comprised of a homopolymer, heteropolymer and/or a blend of such polymers and repeating units may be present other than those depicted by Formula I and Formula Ia.

Polyiminocarbonates are synthesized from dihydroxy and diphenol monomers via one of the appropriate methods disclosed by U.S. Pat. No. 4,980,449, the disclosure of which is incorporated by reference. According to one method, part of the dihydroxy or diphenol compound is converted to the appropriate dicyanate, then, equimolar quantities of the dihydroxy or diphenol compound and the dicyanate are polymerized in the presence of a strong base catalyst such as a metal alkoxide or metal hydroxide.

The monomers compounds of formula IV and formula IVa may also be reacted with phosgene or phosgene-like reactants to form polycarbonates with —O—C(=O)—O— linkages. The method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are also incorporated herein by reference. Because $X_1$ and $X_3$ are independently selected from O, S and $NR_3$, the reaction of the formula IV and formula IVa monomers with phosgene will also produce urethane linkages (—$NR_3$—(C=O)—$NR_3$—), carbonodithioate linkages (—S—(C=O)—S—), carbamate linkages (—O—(C=O)—$NR_3$—), thiocarbonate linkages (—S—(C=O)—O—) and thiocarbamate linkages (—S—(C=O)—$NR_3$—).

Other methods adaptable for use to prepare the polycarbonate and other phosgene-derived polymers of the present invention are disclosed in U.S. Pat. Nos. 6,120,491, and 6,475,477 the disclosures of which are incorporated by reference. The polycarbonates and other phosgene derivatives may also be prepared by dissolving the Formula IV and/or Formula Iva monomer in methylene chloride containing 0.1M pyridine or triethylamine. A solution of phosgene in toluene at a concentration between about 10 and about 25 wt %, and preferably about 20 wt %, is added at a constant rate, typically over about two hours, using a syringe pump or other means. The reaction mixture is quenched by stirring with tetrahydrofuran (THF) and water, after which the polymer is isolated by precipitation with isopropanol. Residual pyridine (if used) is then removed by agitation of a THF polymer solution with a strongly acidic resin, such as AMBERLYST 15.

The monomer compounds of Formula IV and/or Formula IVa may also be directly reacted with aliphatic or aromatic dicarboxylic acids in the carbodiimide mediated process disclosed by U.S. Pat. No. 5,216,115 using 4-(dimethylamino) pyridinium-p-toluene sulfonate (DPTS) as a catalyst to form the aliphatic or aromatic poly(ester amides) when both $X_3$ groups are O. The disclosure of U.S. Pat. No. 5,216,115 is incorporated by reference. Dicarboxylic acids according to one embodiment of the present invention have the structure of Formula VII:

$$HOOC-R_5-COOH \quad (VII)$$

in which, for the aliphatic copolymers, $R_5$ is selected from saturated and unsaturated, substituted and unsubstituted alkyl or heteroalkyl groups containing up to 30 carbon atoms, and preferably from 2 to 12 carbon atoms. Heteroalkyl groups contain up to eight N, O, P or S atoms. For aromatic copolymers $R_5$ is selected from aryl and alkylaryl groups containing up to 24 carbon atoms and preferably from 13 to 20 carbon atoms, and optionally may also include up to eight N, O, P or S atoms. For both aliphatic and aromatic copolymers, N-heteroatoms may be N-substituted to reduce polymer $T_g$ and melt viscosity.

The process forms polymers with $-X_3-C(=O)-R_5-C(=O)-X_1-$ linkages, $R_5$ may be selected so the dicarboxylic acids employed as the starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_5$ of formula VII is $-CH_2-CH_2-C(=O)-$, $-CH_2-CH_2-$, $-CH=CH-$ and $-CH_2-C(=O)-$, respectively).

Another naturally-occurring aliphatic dicarboxylic acid is adipic acid ($R_5$ is $(-CH_2-)_4$), found in beet juice. Still yet another biocompatible aliphatic dicarboxylic acid is sebacic acid ($R_5$ is $(-CH_2-)_8$), which has been studied extensively and has been found to be nontoxic as part of the clinical evaluation of poly(bis(p-carboxyphenoxy)propane-co-sebacic acid anhydride) by Laurencin et al., J. Biomed. Mater. Res., 24, 1463-81 (1990).

Other biocompatible aliphatic dicarboxylic acids include oxalic acid ($R_5$ is a bond), malonic acid ($R_5$ is $-CH_2-$), glutaric acid ($R_5$ is $(-CH_2-)_3$), pimelic acid ($R_5$ is $(-CH_2-)_5$), suberic acid ($R_5$ is $(-CH_2-)_6$) and azelaic acid ($R_5$ is $(-CH_2-)_7$). $R_5$ can thus represent $(-CH_2-)_Q$, where Q is between 0 and 8 inclusive. Among the suitable aromatic dicarboxylic acids are terephthalic acid, isophthalic acid and bis(p-carboxy-phenoxy) alkanes such as bis(p-carboxyphenoxy) propane.

$R_5$ can also have the structure of Formula VIII:

$$-(CH_2-)_aO-[(CH_2-)_aCHR_4-O-]_m(CH_2-)_a \quad (VIII)$$

wherein a is from 1 to 3, inclusive, m is from 1 to 500,000, inclusive, and $R_4$ is hydrogen or a lower alkyl group containing from one to four carbon atoms. $R_4$ is preferably hydrogen, a is preferably 1, and m is preferably between about 10 and about 100, and more preferably between about 10 and about 50.

The diacids of Formula VIII are formed by the oxidation of poly(alkylene oxides) according to well-known methods. One example of such a compound is biscarboxymethyl poly (ethylene glycol), which is commercially available.

$R_5$ can also have the structure of Formula IX:

$$-R_3-C(=O)-O[(-CH_2)_a-CHR_4-O-]_mC(=O)-R_3 \quad (IX)$$

wherein a, m and $R_4$ and the preferred species thereof are the same as described above with respect to Formula VIII. $R_3$ is selected from a bond or straight and branched alkyl and alkylaryl groups containing up to 30 carbon atoms, including embodiments containing up to 18 carbon atoms.

The dicarboxylic acids of Formula IX are poly(alkylene oxides)bis-functionalized with dicarboxylic acids having the structure of Formula VII wherein $R_5$ is the same as described above for Formula VII and preferably contains up to 12 carbon atoms.

The poly(alkylene oxides) of Formula IX that are bis-functionalized with dicarboxylic acids are prepared by the reaction of a non-functionalized poly(alkylene oxide) with an excess of either the dicarboxylic acid (mediated by a coupling agent such as dicyclohexyl carbodiimide), the anhydride (e.g. succinic anhydride) in the presence of pyridine or triethylamine, or a di carb-oxylic acid chloride (e.g. adipoyl chloride) in the presence of an acid acceptor like triethylamine.

Polymers prepared from the Formula IV and Formula IVa starting materials of the present invention with at least one bromine- or iodine-substituted aromatic ring are radio-opaque, such as the polymers prepared from radiopaque diphenol compounds prepared according to the disclosure of U.S. Pat. No. 6,475,477, as well as he disclosure of co-pending and commonly-owned U.S. patent application Ser. No. 10/592,202, the disclosures of both of which are incorporated herein by reference. The iodinated and brominated diphenol monomers of the present invention can also be employed as radio-opacifying, biocompatible non-toxic additives for other polymeric biomaterials.

Bromine and iodine substituted aromatic monomers of the present invention are prepared by well-known iodination and bromination techniques that can be readily employed by those of ordinary skill in the art guided by the above referenced granted patent and pending application (now published) without undue experimentation. The halogenated aromatic compounds from which the halogenated aromatic monomers of the present invention are prepared undergo ortho-directed halogenation. The term, "ortho-directed", is used herein to designate orientation of the halogen atom(s) relative to the $X_1$ group of the DAT or DAT analog, or the $X_3$ group if the amino acid has an aromatic ring.

Random or block copolymers of the Formula I, Formula Ia, Formula II and Formula IIa polymers of the present invention with a poly(alkylene oxide) may be prepared according to the method disclosed in U.S. Pat. No. 5,658,995, the disclosure of which is also incorporated by reference. The poly(alkylene oxide) is preferably a poly(ethylene glycol) block/unit typically having a molecular weight of less than about 10,000 per unit. More typically, the poly(ethylene glycol) block/unit has a molecular weight less than about 4000 per unit. The molecular weight is preferably between about 1000 and about 2000 per unit.

The molar fraction of poly(ethylene glycol) units in block copolymers may range from greater than zero to less than 1, and is typically greater than zero up to about 0.5, inclusive.

More preferably the molar fraction is less than about 0.25 and yet more prefer-ably less than about 0.1. In more preferred variations, the molar fraction may vary from greater than about 0.001 to about 0.08, and most preferably, between about 0.025 and about 0.035.

Unless otherwise indicated, the molar fractions reported herein are based on the total molar amount of poly(alkylene glycol) and non-glycol units in the polymers The polymer glass transition temperature tends to increase as the degree of halogenation and the molar fraction of free carboxylic acid units increase. Higher weight percentages of poly(alkylene oxide) are typically used in polymers with higher levels of iodination or with higher molar fractions of free carboxylic acid units to maintain the polymer glass transition temperature within the desired range for the end use application. N-alkylation provides an alternative means for lowering the polymer glass transition temperature so that the amount of poly(alkylene oxide) may be lowered or eliminated without adversely affecting the polymer melt properties.

The Formula I, Formula Ia, Formula II and Formula IIa polymers have weight-average mollecular weights above about 20,000, preferably above 40,000 and more preferably above about 80,000, calculated from gel permeation chromatography (GPC) relative to polystyrene standards using tetrahydrofuran (THF) as the eluent without further correction. Stated another way, the polymers preferably have between about 30 and 50 of the repeating units depicted in Formula I, Formula Ia, Formula II and Formula IIa.

The polymers of the present invention are defined as including polymers polymerized from formula IV and formula IVa monomers having pendent free carboxylic acid groups ($R_4$=H). However, it is not possible to polymerize polymers having pendent free carboxylic acid groups from corresponding monomers with pendent free carboxylic acid groups without cross-reaction of the free carboxylic acid group with the co-monomer. Accordingly, polymers in accordance with the present invention having pendent free carboxylic acid groups are prepared from homopolymers and copolymers of benzyl and tert-butyl ester monomers of the present invention having the structure of formula IV or formula IVa in which $R_4$ is a benzyl or tert-butyl group.

The benzyl ester homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491, the disclosure of which is incorporated herein by reference. The tert-butyl ester homopolymers and copolymers may be converted to corresponding free carboxylic acid homopolymers and copolymers through the selective removal of the tert-butyl groups by the acidolyis method disclosed by U.S. application Ser. No. 10/592,202, also incorporated herein by reference. The catalytic hydrogenolysis or acidolysis is necessary because the lability of the polymer backbone prevents the employment of harsher hydrolysis techniques.

The molar fraction of free carboxylic acid units in the polymers of the present invention can be adjusted according to the present invention to modify the degradation of devices made from such polymers. For example, polymers with lower amounts of free carboxylic acid will have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are required.

After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer thermo-forming techniques such as extrusion and injection molding when the degradation temperature of the polymer is above the glass transition or crystalline melt temperature, or conventional non-thermal techniques can be used, such as compression molding, injection molding, solvent casting, spin casting, wet spinning Combinations of two or more methods can be used. Shaped articles prepared from the polymers are useful, inter alia, as degradable biomaterials for medical implant applications.

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like. Further, stents may be comprised of at least one fiber material, curable material, laminated material, and/or woven material. The medical device may also be a stent graft or a device used in embolotherapy.

Details of stent products and fabrication in which the polymers of the present invention may be employed are disclosed in co-pending and commonly-owned U.S. patent application Ser. No. 10/952,202 filed Sep. 27, 2004, the disclosure of which is incorporated by reference. Stents are preferably fabricated from the radiopaque polymers of the present invention, to permit fluoroscopic positioning of the device.

The highly beneficial combination of properties associated with the polymers provided by the present invention means these polymers are well-suited for use in producing a variety of resorbable medical devices besides stents, especially implantable medical devices that are preferably radiopaque, biocompatible, and have various times of bioresorption. Polymers are provided that are biocompatible for their intended end use and degrade under physiological conditions into degradation products that are also non-toxic in the intended end use of the polymer.

For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the resorbable polymers of the present invention are well-suited for use in producing a variety of coatings for medical devices, especially implantable medical devices.

Further, in some preferred embodiments, the present polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other resorbable devices that can be advantageously formed from the polymers of the present invention, include devices for use in tissue engineering. Examples of suitable resorbable devices include tissue engineering scaffolds and grafts (such as vascular grafts, grafts or implants used in nerve regeneration). The present resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various resorbable devices useful in dental applications may advantageously be formed according to embodiments of the present invention. For example devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

The polymers of the present invention are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which the polymers of the present invention may be employed are disclosed in co-pending and commonly-owned U.S. patent application Ser. No. 10/952,274 filed Sep. 27, 2004, the disclosure of which is incorporated by reference. Embolotherapy treatment methods are by their very nature local rather than systemic and the products are preferably fabricated from the radiopaque polymers of the present invention, to permit fluoroscopic monitoring of delivery and treatment.

The present polymers are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material and processed biologic materials, and the like. Any number of transport systems capable of delivering therapeutics to the body can be made, including devices for therapeutic delivery in the treatment of cancer, intravascular problems, dental problems, obesity, infection, and the like.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dis-persed within a polymeric matrix or physically admixed with a polymer of the present invention. Controlled therapeutic agent delivery systems may also be prepared by direct application of the therapeutic agent to the surface of an implantable medical device such as a bioresorbable stent device (comprised of at least one of the present polymers) without the use of these polymers as a coating, or by use of other polymers or substances for the coating.

When $R_4$ is hydrogen, the $COOR_4$ pendant groups of the polymers of the present invent-tion may also be derivatized by the covalent attachment of a therapeutic agent. Depending upon the moieties present on the underivatized therapeutic agent, the covalent bond may be an amide bond or an ester bond. Typically, the therapeutic agent is derivatized at a primary or secondary amine, hydroxyl, ketone, aldehyde or carboxylic acid group. Chemical attachment procedures are described by U.S. Pat. Nos. 5,219,564 and 5,660,822; Nathan et al., Bio. Cong. Chem., 4, 54-62 (1993) and Nathan, Macromol., 25, 4476 (1992), the disclosures of which are incorporated by reference.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymers of the present invention using conventional techniques well-known to those of ordinary skill in the art. For this therapeutic agent delivery embodiment, it is not essential that the polymer have pendent groups for covalent attachment of the therapeutic agent.

The polymer compositions of the present invention containing therapeutic agents, regard-less of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a thera-peutic agent to the site of implantation by being fabricated from or coated with the therapeutic agent delivery system of the present invention in which a polymer of the present invention has a therapeutic agent physically admixed therein or covalently bonded thereto, such as a drug-eluting stent. Embolotherapeutic particles may also be fabricated for delivery of a therapeutic agent.

Examples of biologically or pharmaceutically active therapeutic agents that may be cova-lently attached to the polymers of the present invention include acyclovir, cephradine, procaine, ephedrine, adriamycin, daunomycin, plumbagin, atropine, quinine, digoxin, quinidine, bio-logically active peptides, chlorin $e_6$, cephradine, cephalothin, proline and proline analogs such as cis-hydroxy-L-proline, malphalen, penicillin V and other antibiotics, aspirin and other non-steroidal anti-inflammatories, nicotinic acid, chemodeoxycholic acid, chlorambucil, anti-tumor and anti-proliferative agents, including anti-proliferative agents that prevent restenosis, hormones such as estrogen, and the like. Biologically active compounds, for the purposes of the present invention, are additionally defined as including cell attachment mediators, biologically active ligands, and the like.

The invention described herein also includes various pharmaceutical dosage forms containing the polymer-therapeutic agent combinations of the present invention. The combination may be a bulk matrix for implantation or fine particles for administration by traditional means, in which case the dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids, etc.

The dosage forms may include one or more pharmaceutically acceptable carriers. Such materials are non-toxic to recipients at the dosages and concentrations employed, and include dil-uents, solubilizers, lubricants, suspending agents, encapsulating materials, penetration enhancers, solvents, emollients, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counter-ions such as sodium and/or nonionic surfactants such as tween, pluronics or PEG.

Therapeutic agents to be incorporated in the polymer conjugates and physical admixtures of the invention may be provided in a physiologically acceptable carrier, excipient stabilizer, etc., and may be provided in sustained release or timed release formulations supplemental to the polymeric formulation prepared in this invention. Liquid carriers and diluents for aqueous dispersions are also suitable for use with the polymer conjugates and physical admixtures.

Subjects in need of treatment, typically mammalian, using the polymer-therapeutic agent combinations of this invention, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations of this invention may be prepared for storage under conditions suitable for the preservation of therapeutic agent activity as well as maintaining the integrity of the polymers, and are typically suitable for storage at ambient or refrigerated temperatures.

Depending upon the particular compound selected, transdermal delivery may be an option, providing a relatively steady delivery of the drug, which is preferred in some circumstances. Transdermal delivery typically involves the use of a compound in solution, with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulations of this invention may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally or via inhalation. Therapeutic agent toxicity could thus be reduced by selective delivery to the affected site. For example if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequently, the toxicity and side effects associated with higher dosages.

Therapeutic agents incorporated into the polymers of this invention may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations of this invention may also be formed into shaped articles, such as valves, stents, tubing, prostheses, and the like. Cardiovascular stents may be combined with therapeutic agents that prevent restenosis. Implantable medical devices may be combined with therapeutic agents that prevent infection.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate from the formulations of this invention is also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods of this invention, the polymer-therapeutic agent combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

A major advantage of using the radiopaque, bioresorbable polymers of the instant invention in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

Example 1

Preparation of the Ethyl Ester of Amino Acids

Ethyl esters of amino acids were prepared by reaction of the amino acid with ethanol and thionyl chloride as described in a literature procedure (Bodanszky, Practice of Peptide Synthesis (Springer-Verlag, New York 1984). The products were characterized using HPLC, $^1$H NMR, elemental analysis and melting point. In most cases esters were used as the hydrochloride salt with in situ free base generation with triethylamine. Free bases of the esters were also prepared and isolated in some cases by treating with 5M aqueous potassium carbonate. When available esters were obtained from commercial sources.

Example 2

Synthesis of Desaminotyrosyl Serine Ethyl Ester

To a single-necked 500 mL round-bottomed flask equipped with an addition funnel and a magnetic stirrer was added 3-(4-hydroxyphenyl)propionic acid (10.0 g, 60.2 mmol), serine-ethyl ester hydrochloride (10.7 g, 63.2 mmol), hydroxybenzotriazole hydrate (0.81 g, 6.0 mmol), and tetrahydrofuran (50 mL). The flask was cooled in an ice-water bath and triethylamine (8.85 mL, 63.4 mmol) was added drop wise over a period of 10 minutes and the reaction mixture was stirred for 30 more minutes and then 1-ethyl-3-[3-(dimethylamino)propyl]carbodiimide hydrochloride (12 g, 50 mmol) was added and stirred at ice-water bath temperature for 1 hour.

The reaction mixture was further stirred at room temperature for 4 hours. Distilled water (150 mL) was added to the reaction flask and was transferred to a separatory funnel and extracted twice with 100 mL ethyl acetate. The combined extract was washed twice with 0.2 M hydrochloric acid solution (100 mL), twice with 0.5 M sodium bicarbonate solution (100 mL). After drying over anhydrous magnesium sulfate and stirring with 100-mesh activated carbon, the solution was filtered. Solvent was removed by rotary evaporation and the monomer was dried under vacuum. The syrupy product obtained was stirred with hexane (100 mL) for 6 h. The product was obtained as white powder (yield 72%). The identity of the product as desamino-tyrosyl serine ethyl ester was con-firmed by elemental analysis and $^1$H NMR spectroscopy and had a melting point of 85-88° C.

Examples 3 and 4

Synthesis of DAT-Hydroxyproline Ethyl Ester and DAT-Threonine Ethyl Ester

Using the procedure of Example 2, ethyl esters of trans-hydroxyproline and threonine were coupled to desaminotyrosine. The resulting monomers were characterized as in Example 1 by elemental analysis, $^1$H NMR spectroscopy and HPLC.

| Table of reagents used for the preparation of monomers (DAT-AA ethyl ester) | | | | | | |
|---|---|---|---|---|---|---|
| Amino acid | AA-ethyl ester•HCl, (g) | DAT (g) | HOBt (g) | Triethyl-amine (g) | EDCI (g) | Yield (%) |
| Serine | 21.43 | 20 | 1.63 | 12.8 | 25.4 | 49.3 |
| Threonine | 5.22 | 4.5 | 0.37 | 2.88 | 5.71 | 54.0 |
| tHyp | 9.89 | 8.0 | 0.65 | 5.12 | 10.2 | 43.3 |
| 5-HTrp | 5.23 | 2.9 | 0.24 | 1.86 | 3.69 | 69.8 |
| Thyronine | 0.65* | 0.34 | 0.03 | — | 0.43 | 61.2 |

*thyronine ethyl ester free base was used

Examples 5 and 6

Synthesis of I$_2$DAT-Thyronine Ethyl Ester and I$_2$DAT-5-Hydroxytryptophan Ethyl Ester Thyronine ethyl ester hydrochloride and 5-hydroxytryptophan ethyl ester hydrochloride were prepared and converted to the corresponding free base with 5M aqueous potassium carbonate solution. Using the procedure of Example 2, thyronine ethyl ester and 5-hydroxytryptophan ethyl esters were coupled with diiodo-DAT {3-(3,5-diiodo-4-hydroxyphenyl))propionic acid} to get the corresponding diiodinated monomers. The monomers were also characterized as in Example 2.

Table of reagents used for the iodinated monomers (I₂DAT-AA ethyl esters)

| Amino acid | AA-ethyl ester | I₂DAT | IIOBt | Triethyl-amine | EDCI | % yield |
|---|---|---|---|---|---|---|
| tHyp | 9.8 | 20 | 0.65 | 5.08 | 10.1 | 65 |
| 5-HTrp | 8.05 | 11.28 | 0.36 | 2.87 | 5.69 | 54 |
| Thyronine | 5.07* | 6.57 | 0.21 | — | 3.33 | 57 |

*thyronine ethyl ester free base was used

Example 7

Polymerization of Diiododesaminotyrosyl Thyronine Ethyl Ester Using Triphosgene

In a 100 mL round-bottomed flask equipped with a magnetic stirrer and a syringe pump, were placed 1.5 g (2.1 mmol) diiododesaminotyrosyl thyronine ethyl ester, 15 mL of methylene chloride, and 0.66 g (8.3 mmol) of pyridine, the resulting solution was stirred and to the stirred solution was added 0.25 gram of triphosgene dissolved in 1 mL of methylene chloride over a period of 3 h using a syringe pump. The product was isolated by precipitation with 2-propanol. The product was dried in vacuum oven at 40° C. and characterized by GPC (Mw=65 KDa) and DSC (glass transition temperature=67° C.) and by $^1$H NMR spectroscopy. This polymer could be compression molded into thin films using a hot press. The compression molded films showed a tensile modulus of ca 290 kpsi and yield stress of 10.9 kpsi.

Example 8

Copolymer of DTE and DAT-5-Hydroxytryptophan Ethyl Ester (DHTrpE)

Into a 100 mL round bottomed flask were added 2.5 g (7.0 mmol) of DTE and 2.5 g of DHTrpE. To the flask were added 30 mL of methylene chloride and 6.1 mL of pyridine. Most of the solid dissolved. However, some turbidity was present. This was filtered with a coarse fluted filter paper into a 3-necked 100 mL round bottomed flask. 1.42 g of triphosgene in 10 mL of methylene chloride was added over 3 h. The reaction mixture became viscous. It was quenched with 10 mL of 9:1 THF-water. The product was isolated by precipitation with IPA followed by 3 washings with IPA in a laboratory blender. The product was dried under a stream of nitrogen and then in vacuum oven. The $^1$H NMR spectrum showed a ratio of 1:0.7 of DTE to DHTrpE. The Tg of the polymer was 114° C.

Another polymerization was also carried out using a 3:1 ratio of DTE (3 g) and DAT-5-hydroxytryptopan ethyl ester (1 g). In this case a clear solution was obtained and therefore the polymerization was carried out without filtration. $^1$H NMR spectrum of the polymer confirmed 3:1 ratio of DTE to DHTrpE and the Tg of the polymer was 105° C.

Example 9

Wet Tg and Dry Tg of All the New AA Polymers

Glass transition temperature of the polymers was determined by differential scanning calorimetry from the second heat. The wet Tgs of the polymers were measured using differential mechanical analyzer (DMA). For this measurement a compression molded film of the polymer were used. In some cases a film could not he obtained or the film was too brittle to make a measurement. In such cases only the dry Tg is reported.

Table showing the dry and wet Tgs of the polymers from the monomers as shown

| Monomer | Dry Tg, ° C. | Wet Tg, ° C. |
|---|---|---|
| DAT-serine ethyl ester | 58 | 18-19 |
| DAT-threonine ethyl ester | 75 | 46 |
| DAT-trans-Hydroxyproline ethyl ester | 103 | >50 |
| DAT-5-hydroxytryptophan ethyl ester: DTE (0.7:1) | 94 | 43 |
| DAT-5-hydroxytryptophan ethyl ester: DTE (1:3) | 92 | 40 |
| DAT-Thyronine ethyl ester | 84 | 43 |
| I₂DAT-trans-IIydroxyproline ethyl ester | 155 | >70 |
| I₂DAT-Thyronine ethyl ester | 132 | >70 |

Example 10

Determination of Solubility of Monomers

About 30 mg of the monomer and 2 mL of PBS (pH 7.4) were added to a 2 dram vial. The vial was agitated on a vortex mixer for 2 h. If all the solid dissolved, more solid was added and agitation was continued. The mixture was filtered using a syringe filter to remove undissolved monomer. The clear filtrate was analyzed by HPLC by injecting 5 microliter of the filtrate. The area of the peak obtained was measured. A calibration curve was obtained by injecting known concentration of the monomer in methanol and plotting concentration against the area of the peaks obtained. Using this calibration curve the solubility of the monomer in PBS at ambient temperature was determined.

To determine the solubility at 37° C., the vials were placed in an incubator at 37° C. for 2 h. The mixture was then quickly filtered using syringe filter and then diluted 2× with PBS to prevent precipitation of the monomer. The solubility is determined using procedures similar to that used at room temperature solubility.

Table showing the solubility of the monomers prepared above in PBS at 25° C.*

| Monomer | Solubility, mg/mL, 25° C. | Solubility, mg/mL, 37° C. |
|---|---|---|
| DAT-tyrosine ethyl ester (DTE) | 0.74 | NA |
| DAT-serine ethyl ester | 7.7 | 14.13 |
| DAT-threonine ethyl ester | 10 | NA |
| DAT-trans-Hydroxyproline ethyl ester | 12 | NA |
| DAT-5-hydroxytryptophan ethyl ester | 0.15 | 0.43 |
| DAT-Thyronine ethyl ester | <0.05 | NA |

*with most monomers a small amount of the byproducts of the reaction were present.

Example 11

Preparation of β-Hydroxy Leucine

β-Hydroxy leucine is prepared using the method of Adam J. Morgan and co-workers (Morgan et al., Org. Lett, 1, 1949-1952 (1999).

Example 12

β-Hydroxy Leucine Ethyl Ester Hydrochloride

Into a 100 mL round-bottomed flask equipped with reflux condenser is added 50 mL ethanol and stirred using magnetic stirrer under positive nitrogen pressure. The flask is cooled using a dry ice/IPA bath to −35° C. Using an addition funnel 8.5 mL (0.12 mol) of thionyl chloride is added over 10 min. To the flask is then added 14.7 g (0.1 mol) of β-Hydroxy Leucine. The cooling bath is then removed and the flask heated using a heating mantle to reflux for 10 h. The reaction mixture is concentrated to 20 mL and then precipitated by adding 50 mL of ether. The product is isolated by filtration and washed with ether. The product β-Hydroxy Leucine ethyl ester hydrochloride is characterized by proton NMR and elemental analysis.

Example 13

Preparation of DAT-β-Hydroxy Leucine Ethyl Ester

Into a 250 mL round bottomed flask equipped with an overhead stirrer, and a thermometer are added 16.6 g (0.100 mol) of desaminotyrosine, 21.8 g (0.103 mol) of β-Hydroxy Leucine ethyl ester hydrochloride, 1.3 g (0.010 mol) hydroxybenzotriazole, and 120 mL of tetrahydrofuran. The flask is cooled using an ice-water bath to about 5° C. To the flask are then added 10.5 g (0.103 mol) of triethylamine over 5 min followed by 21.1 g (0.11 mol) of EDCI. The reaction mixture is stirred at 5-10° C. for 1 h and then at ambient temperature for 5 h.

To the reaction mixture is then added 240 mL of 0.2 M HCl and stirred for 10 min. It is then transferred to a 50 mL separatory funnel and extracted with 500 mL of ethyl acetate. The aqueous layer is separated and discarded. The organic layer is washed with 250 mL of 0.02 M HCl, 5% aqueous NaHCO₃ and 250 mL 20% aqueous NaCl. After drying over MgSO₄ it is evaporated to dryness and the viscous oil is stirred with hexane till it solidifies. The product is characterized 1H NMR, HPLC, and elemental analysis. The solubility of the monomer in PBS is also determined as described above.

Example 14

Polymerization of DAT β-Hydroxy Leucine Ethyl Ester

Into a 100 mL round bottomed flask are added 6.45 g (20.0 mmol) of DAT β-Hydroxy Leucine ethyl ester, 40 mL of methylene chloride and 5.93 mL (75.0 mmol) of pyridine. To the resulting mixture with stirring is added 2.18 g (7.33 mmol) of triphosgene in 10 mL of methylene chloride over 3 h using a syringe pump. The reaction mixture is quenched with 5 mL of 9:1 THF-water. The polymer is precipitated with IPA followed by 3 washings with IPA in a laboratory blender. Polymer is isolated by filtration and dried under a stream of nitrogen and then in vacuum oven at 40° C. It is characterized by NMR, DSC (Tg), and mechanical properties.

The foregoing illustrates the novel classes of monomers and bioresorbable polymers derived therefrom with varying mechanical properties that hydrolytically degrade under physiological conditions and resorb at varying rates. The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A polymer comprising at least 10 mol % of repeating units having a structure selected from the group consisting of Formula (I) and Formula (Ia)

for which the variables are defined as follows:

Ar is a phenylene ring optionally substituted with from one to four substituents independently selected from the group consisting of halogen, halomethyl, halomethoxy, methyl, methoxy, thiomethyl, nitro, sulfoxide and sulfonyl;

$R_1$ is selected from the group consisting of a bond and optionally substituted alkylene, heteroalkylene, alkenylene and heteroalkenylene groups containing from one to ten carbon atoms;

$X_1$, $X_2$ and $X_3$ are independently selected from the group consisting of O, S and $NR_3$;

$R_2$ is selected from the group consisting of hydrogen and alkyl groups containing from one to thirty carbon atoms, or $R_{2a}$ is an alkylene group covalently bonded to both the $NR_2$ nitrogen atom and AA, so that —N—$R_{2a}$-AA- defines a heterocyclic ring;

$R_3$ is selected from the group consisting of hydrogen and alkyl groups containing from one to thirty carbon atoms;

AA has a pendant $COOR_4$ group in which $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000; and

AA and $X_3H$ of Formula (I) are selected so that ($R_2$—HN-) AA-$X_3H$ defines an —$X_3H$ substituted amino acid which is not tyrosine, and AA and $X_3H$ of Formula (Ia) are selected so that defines an $X_3H$-substituted amino acid;
wherein said polymer has a glass transition temperature or crystalline melting temperature greater than 37° C. when fully hydrated in phosphate buffered saline (PBS) (0.1 M, pH 7.4) at 37° C. and said Formula (I) and (Ia) variables are selected so that monomers comprising said Formula (I) and Formula (Ia) repeating units have a solubility in said PBS solution at 37° C. of at least about 3 mg/mL.

2. The polymer of claim 1, wherein AA and $X_3$ are selected so that defines an amino acid selected from the group consisting of hydroxy-tryptophan, mercapto-tryptophan, hydroxy-proline and mercapto-proline.

3. The polymer of claim 1, wherein said Formula (I) and Formula (Ia) variables are selected to provide a polymer with an equilibrium water content in said PBS solution at 37° C. of less than about 20 wt %.

4. The polymer of claim 1, wherein AA and $X_3H$ of Formula (I) are selected so that ($R_2$—HN-)AA-$X_3H$ defines an alpha-amino acid, and wherein AA and $X_3H$ of Formula (Ia) are selected so that defines an alpha-amino acid.

5. The polymer of claim 4, wherein said alpha-amino acid is a naturally-occurring amino acid.

6. The polymer of claim 4, wherein said alpha-amino acid is an essential amino acid.

7. The polymer of claim 1, comprising two different repeating units having the structures of Formula (I) or Formula (Ia), wherein said polymer comprises a first repeating unit in which $R_4$ is hydrogen, so that $COOR_4$ is a pendant free carboxylic acid group, and a second repeating unit in which $R_4$ is an alkyl group containing up to 30 carbon atoms so that $COOR_4$ is a pendant carboxylate group.

8. The polymer of claim 7, wherein between about 1% and about 50% of the AA groups have pendant free carboxylic acid groups.

9. The polymer of claim 1, wherein at least 50% of the Ar groups are substituted with two to four atoms selected from the group consisting of iodine atoms and bromine atoms.

10. The polymer of claim 1, wherein $R_1$ is —$CH_2$—$CH_2$—.

11. The polymer of claim 1, wherein $X_1$, $X_2$ and $X_3$ are all oxygen.

12. The polymer of claim 1, characterized by being a polycarbonate, polyester, poly(phosphazine), poly(phosphoester), poly(iminocarbonate), polyether, polyurethane, poly(carbamate), poly(thiocarbonate), poly(carbonodithionate) or poly(thiocarbamate).

13. The polymer of claim 1, characterized by being a polyalkylene oxide block copolymer.

14. The polymer of claim 1, wherein $R_1$ is —$CH_2$—$CH_2$— or —CH=CH—, $X_1$, $X_2$ and $X_3$ are O and Ar is a phenylene group optionally substituted with two to four atoms selected from the group consisting of iodine atoms and bromine atoms.

15. The polymer according to claim 1, comprising repeating units having a structure selected from the group consisting of Formula (II) and Formula (IIa):

wherein A is selected from the group consisting of:

wherein $R^{10}$ is selected from the group consisting of H, and optionally substituted alkyl, heteroalkyl, alkenyl and heteroalkenyl groups containing from one to 30 carbon atoms, and $R^{12}$ is selected from the group consisting of optionally substituted alkylene, heteroalkylene, alkenylene and heteroalkenylene groups containing from one to 18 carbon atoms, and alkylarylene, heteroalkylarylene, alkenylarylene and heteroalkenylarylene groups containing from three to 12 carbon atoms.

16. A polymer according to claim 1, further comprising a polyalkylene oxide block repeating unit having a structure according to Formula (III):

wherein B is —O—((CHR$^6$)$_p$—O)$_q$—; each $R^6$ is independently H or $C_1$- to $C_3$-alkyl; p is an integer in the range of one to about 4; q is an integer in the range of one to about 100; and $A^2$ is selected from the group consisting of:

-continued wherein $R^{10}$ is selected from the group consisting of H and optionally substituted alkyl, heteroalkyl, alkenyl and heteroalkenyl groups containing from one to 30 carbon atoms, and $R^{12}$ is selected from the group consisting of optionally substituted alkylene, heteroalkylene, alkenylene and heteroalkenylene groups containing from one to 18 carbon atoms, and alkylarylene, heteroalkylarylene, alkenylarylene and heteroalkenylarylene groups containing from three to 12 carbon atoms.

17. A load-bearing medical implant comprising the polymer of claim 1.

18. A compound having the structure of formula (IV) or formula (IVa):

for which the variables are defined as follows:

Ar is a phenylene ring that optionally substituted with from one to four substituents independently selected from the group consisting of halogen, halomethyl, halomethoxy, methyl, methoxy, thiomethyl, nitro, sulfoxide and sulfonyl;

$R_1$ is selected from the group consisting of optionally substituted alkylene, heteroalkylene, alkenylene and heteroalkenylene groups containing from one to ten carbon atoms;

$X_1$, $X_2$ and $X_3$ are independently selected from the group consisting of O, S and $NR_3$;

$R_2$ is selected from the group consisting of hydrogen and alkyl groups containing from one to thirty carbon atoms bonded only to N, or $R_{2a}$ is an alkylene group covalently bonded to both the $NR_2$ nitrogen atom and AA, so that —N—$R_{2a}$-AA- defines a heterocyclic ring;

$R_3$ is selected from the group consisting of hydrogen and alkyl groups containing from one to thirty carbon atoms;

AA has a pendant $COOR_4$ group in which $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000; and AA and $X_3H$ of Formula (IV) are selected so that ($R_2$—HN-)AA-$X_3H$ defines an —$X_3H$ substituted amino acid which is not tyrosine, and AA and $X_3H$ of Formula (IVa) are selected so that defines an $X_3H$-substituted amino acid;
wherein said Formula (IV) and Formula (IVa) variables are selected so that said compound has a solubility in phosphate buffered saline (PBS) (0.1 M, pH 7.4) at 37° C. greater than about 3 mg/mL.

* * * * *